United States Patent [19]

Harrison

[11] 4,316,453

[45] Feb. 23, 1982

[54] PORTABLE BODY ELECTRODE

[75] Inventor: William H. Harrison, Woodland Hills, Calif.

[73] Assignee: Donald L. Morton & Associates, Pacific Palisades, Calif.

[21] Appl. No.: 106,667

[22] Filed: Dec. 26, 1979

[51] Int. Cl.³ ............................................. A61N 1/40
[52] U.S. Cl. .................................... 128/1.3; 128/804; 219/10.79
[58] Field of Search ................................. 128/1.3–1.5, 128/783, 802, 804; 219/10.79

[56] References Cited

U.S. PATENT DOCUMENTS 636,093  10/1899  Whitfield ............................. 128/1.5
2,502,865  4/1950  Lund ............................... 128/804 X

FOREIGN PATENT DOCUMENTS 759065  11/1933  France ............................. 128/804

Primary Examiner—Lee S. Cohen
Attorney, Agent, or Firm—Poms, Smith, Lande & Rose

[57] ABSTRACT

An electrode of the type used in the treatment of animal tissue by hyperthermia wherein a self-resonant single turn loop electrode creates a field of electromagnetic energy. The electrode comprises three plate members forming the sides and bottom of a box-like area in which the patient is positioned. The fourth electrode is vertically disposed above the patient and between the two side members being arcuate in shape on the edge adjacent the patient and normal to the other members. The two side members are disconnectable from the back member so that the back member can be positioned beneath a patient's mattress and the side members and arcuate member then placed over the patient in operable position when desired.

12 Claims, 12 Drawing Figures

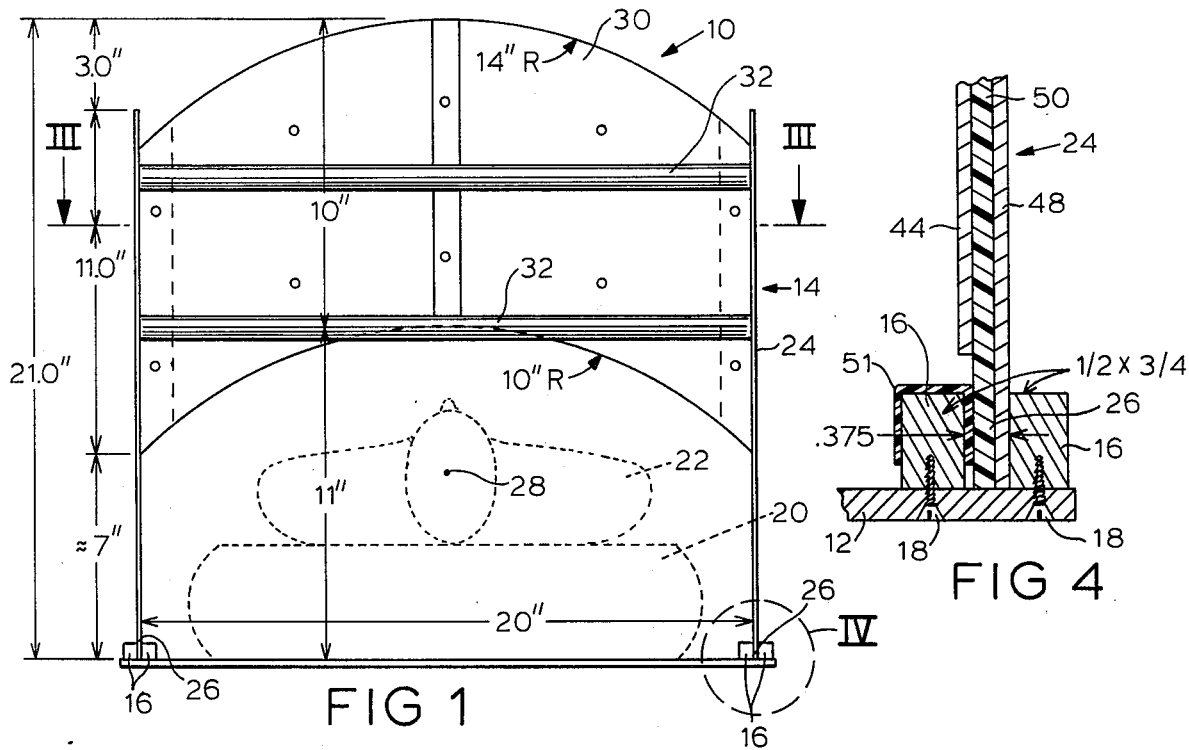
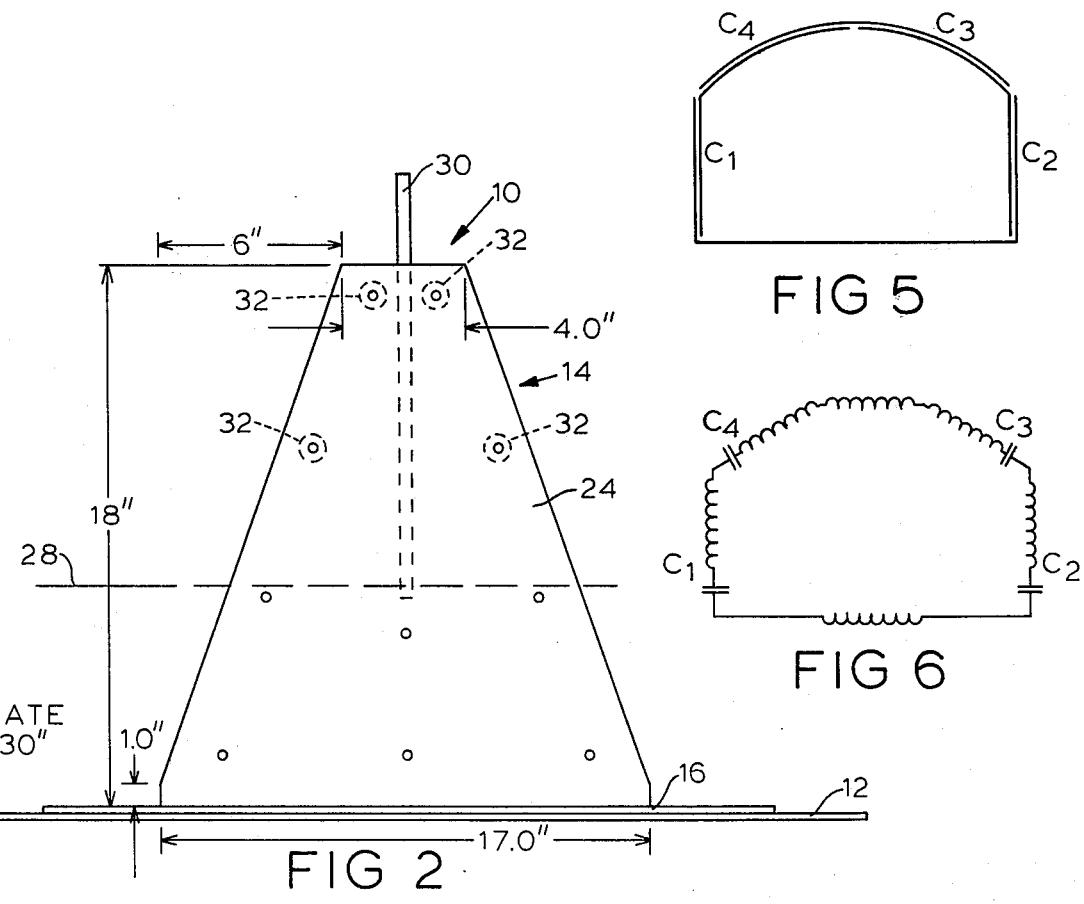

ON AXIS FIELD DISTRIBUTION VS. POSITION

FIG. 11
| LEVEL PWR | X | Y | Z |
|---|---|---|---|
| 1.0 | 0" | 0 | 1.5" |
| .7 | 2 | " | " |
| .33 | 4 | " | " |
| .05 | 6 | " | " |
| .71 | 0" | 0 | 3.0" |
| .56 | 2 | " | " |
| .33 | 4 | " | " |
| .20 | 6 | " | " |
| .12 | 8 | " | " |
| .07 | 10 | " | " |
| .58 | 0" | 0 | 4.5" |
| .47 | 2 | " | " |
| .38 | 4 | " | " |
| .26 | 6 | " | " |
| .17 | 8 | " | " |
| .10 | 10 | " | " |
| .47 | 0 | 0 | 6.0" |
| .44 | 2 | " | " |
| .33 | 4 | " | " |
| .26 | 6 | " | " |
| .17 | 8 | " | " |
| .11 | 10 | " | " |
| .44 | 0 | 0 | 9.0" |
| .43 | 2 | " | " |
| .39 | 4 | " | " |
| .32 | 6 | " | " |
| .25 | 8 | " | " |
| .18 | 10 | " | " |
| LEVEL PWR | X | Y | Z |
|---|---|---|---|
| .44 | 0" | 0" | 11.5" |
| .42 | 2 | " | " |
| .38 | 4 | " | " |
| .30 | 6 | " | " |
| .24 | 8 | " | " |
| .18 | 10 | " | " |
| 1.00 | 0" | 4" | 1.5" |
| .55 | 2 | " | " |
| .12 | 4 | " | " |
| .02 | 6 | " | " |
| .71 | 0 | 4" | 3.0" |
| .54 | 2 | " | " |
| .33 | 4 | " | " |
| .22 | 6 | " | " |
| .13 | 8 | " | " |
| .07 | 10 | " | " |
| .58 | 0 | 4" | 4.5" |
| .50 | 2 | " | " |
| .38 | 4 | " | " |
| .26 | 6 | " | " |
| .17 | 8 | " | " |
| .09 | 10 | " | " |
| .47 | 0 | 4" | 6.0" |
| .44 | 2 | " | " |
| .38 | 4 | " | " |
| .27 | 6 | " | " |
| .18 | 8 | " | " |
| .13 | 10 | " | " |
| LEVEL PWR | X | Y | Z |
|---|---|---|---|
| .44 | 0 | 4" | 9.0" |
| .43 | 2 | " | " |
| .41 | 4 | " | " |
| .33 | 6 | " | " |
| .26 | 8 | " | " |
| .18 | 10 | " | " |
| LEVEL PWR | A | B | C | H |
|---|---|---|---|---|
| .27 | 1.0" | – | – | – |
| .09 | 2.0" | – | – | – |
| .33 | – | 1.0" | – | – |
| .22 | – | 2.0" | – | – |
| .07 | – | 3.0" | – | – |
| .33 | – | – | 1.0" | – |
| .12 | – | – | 2.0 | – |
| .03 | – | – | 3.0 | – |
| 1.00 | – | – | – | 1" |
| .71 | – | – | – | 3 |
| .57 | – | – | – | 5 |
| .33 | – | – | – | 7 |
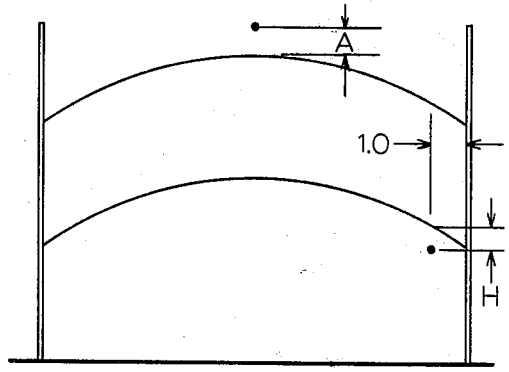
FIG 8
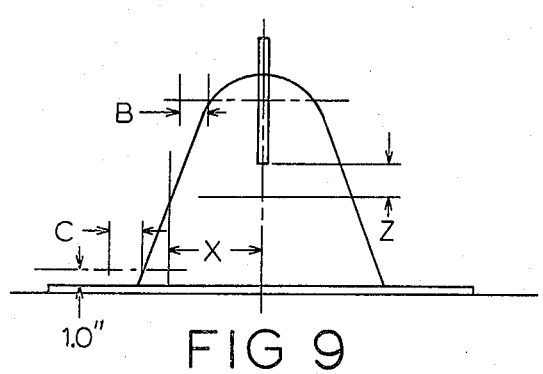
FIG 9
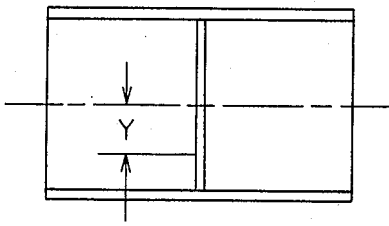
FIG 10

PORTABLE BODY ELECTRODE

BACKGROUND OF THE INVENTION

The present invention relates to electrodes used in medical treatment and, more particularly, to electrodes employed with radio frequency energy to produce deep-heating by hyperthermia.

The therapeutic effect of heat have been known for a long period of time. In particular, it has been found that tumors can be heated and, thereby, destroyed. Likewise, it has been known that radio frequency energy can be employed to cause heating of animal tissue. This has been accomplished by traditional diathermy apparatus.

Recently, in my co-pending application Ser. No. 854,730, filed Nov. 25, 1977 and titled, "Deep Heating Electrode", which has now issued as U.S. Letters Pat. No. 4,186,729, an electrode was shown which allows radio frequency energy to be employed to cause deep heating within an animal body. Prior to my deep heating electrode, a person having a tumor situated deep within his body was unable to have sufficient energy transferred thereto to cause therapeutic heating of the tumor. Before my invention, such heating could only occur by surgically exposing the tumor and placing traditional diathermy electrodes in electrical contact with opposing surfaces of the tissue to cause the energy to pass therethrough.

According to my invention as disclosed in the above-referenced patent, an electrode in the form of a cylinder can be placed about the body of a person over the area of the tumor and deep heating electro-magnetic energy transmitted thereto if the electrode is in the form of a single turn self-resonant loop which causes a series of concentric electro magnetic force lines of substantially equal energy to be created inside the cylinder.

Reference should be made to the above-referenced patent for a more detailed description of the general field to which the present invention relates.

While the cylindrical electrode works for its intended purpose in a great many applications, certain portions of the body create unique problems for which a specialized force field would be desirable. For example, in my co-pending application Ser. No. 097,485, filed Nov. 26, 1979 and titled "Planar disc Magnetic Electrode," an electrode is disclosed particularly adapted for slipping over the head, arm, or leg to create a narrow planar band of energy. This electrode was particularly developed for use in the neck region wherein energy transmitted to the body a few inches above the neck is also transmitted into the brain.

In treating the major body portion with a cylindrical electrode as described in the above-referenced basic patent, some patient discomfort can be created. For example, in extremely weak, bedridden patients, the effort of being positioned within a cylinder can be both physically and psychologically uncomfortable. In many cases, the power level to the tumor region has to be lmited by patient discomfort experienced in the sternum and also coccyx bony regions which are unavoidably simultaneously heated. This is because with a large cylindrical electrode all of the region under the electrode is being heated, whereas the tumor may not be so widely dispersed and could be locally treated if the energy could be directed to that specific area.

Wherefore, it is one objective of the present invention to provide an electrode which is portable. That is, the electrode may be used on any table, metallic or non-metallic, and does not have to be made a part of the table as is the case with the cylindrical electrode.

It is yet another objective of the present electrode to provide an electrode of high convenience. That is, an electrode of two-piece construction where the lower section can be placed on the patient's table while the upper section can be placed over the patient after he is in a prone position.

It is yet another objective of the present invention to provide an electrode having localized heating. That is, one electrode to produce localized heating of the torso thus eliminating some of the problems encountered with previous designs.

SUMMARY

The foregoing objectives have been met in an electrode for use in the treatment of animal tissue by hyperthermia comprising a plurality of plate members of electrically conductive material disposed in overlapped relationship with one another with dielectric material disposed between the overlapped portions to form a self-resonant single turn loop, by the improved electrode comprising a pair of side plate members disposed in parallel spaced relationship with a longitudinal working axis therebetween and parallel to both said side plate members; a back plate member disposed between the side plate members in electrical contact therewith on one side of the working axis and parallel thereto; and, a power plate member disposed between the side plate members in electrical contact therewith on the other side of the working axis and normal thereto.

To provide an even field when placed adjacent the body, the power plate member is arcuate on the edge thereof adjacent to working axis.

To provide for maximum energy transfer in the desired area adjacent the power plate member, the side plate members taper from a width d on the edge adjacent the power plate member to a width of at least 4 d adjacent the back plate member; and, the back plate member is at least 4 d wide.

To provide the convenience, the side plate members are releasable from the back plate member.

In one embodiment as shown, the back plate member is the metallic top of, for example, a gurney cart having electrical connecting means for gripping the edges of the side plate members and for establishing electrical contact along the entire length thereof.

DESCRIPTION OF THE DRAWINGS

FIG. 1 is an end view of the electrode of the present invention in its preferred embodiment.

FIG. 2 is a side view of the electrode of FIG. 1.

FIG. 4 is a cut-away enlarged drawing of the electrode of FIG. 1 in the region IV wherein the side plates releasably connect to the back plate.

FIG. 5 is a simplified drawing of the electrode of FIGS. 1–4 showing the positioning of the capacitive portions thereof.

FIG. 6 is a simplified drawing of the equivalent circuit of the electrode of FIGS. 1–4.

FIGS. 8–10 are simplified drawings of the electrode of the present invention as shown in FIGS. 1–4 with field strength measurement points labelled alphabetically.

FIG. 11 is a table of field measurements of the electrodes of the present invention with various tested values assigned to the alphabetically labelled dimensions of FIGS. 8–10.

DESCRIPTION OF THE PREFERRED EMBODIMENT

Figure 7:
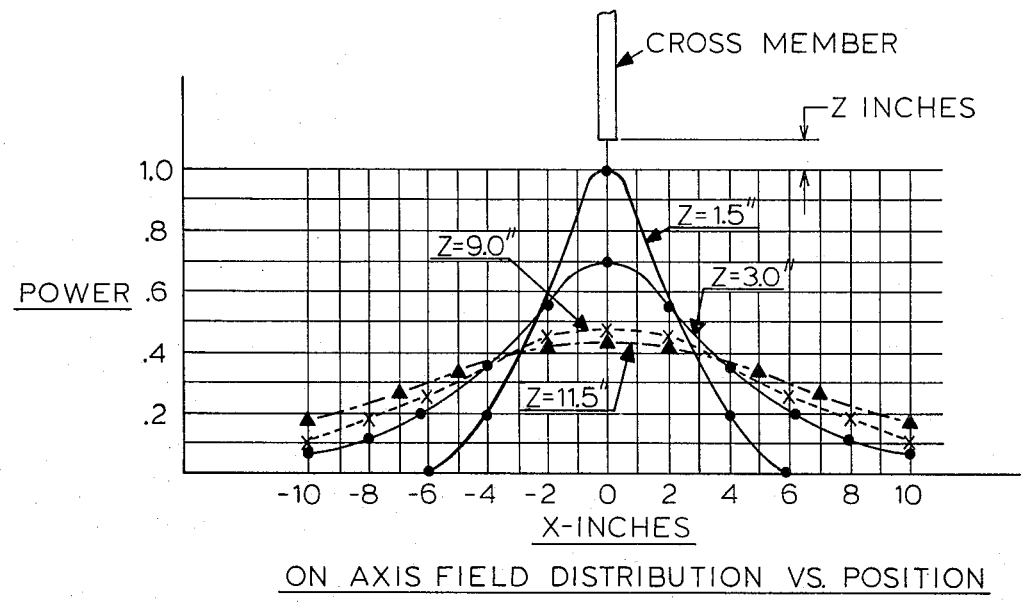
FIG. 7 is a graph of the field distribution versus position within an electrode of the present invention.

Referring first to FIGS. 1–4, an electrode, generally indicated as 10, according to the present invention is shown. Electrode 10 is in two basic pieces, a back plate 12 and an upper assembly generally indicated as 14. The back plate 12 is a flat plate of electrically conductive material such as aluminum, having a pair of spaced guide rails 16 on either side thereof. The drawing figures are dimensioned to indicate the sizes of a tested embodiment discussed hereinafter. As can be seen therefrom, back plate 12 comprises a piece of ¼ inch plate, being a rectangle 20 inches by 30 inches. The guide rails 16 are aluminum bar stock ½ inch by ¾ inch and are attached to the back plate 12 with machine screws 18. It should be understood that the functions of guide rails 16 could also be accomplished by providing slots in back plate 12 as an alternative.

Being thus constructed, back plate 12 is easily adaptable for sliding beneath the mattress 20 upon which a patient 22 is reclining. Thus, treatment can be made without removing the patient 22 from his or her hospital bed if such is desired or required.

The upper assembly 14 comprises a pair of side plates 24 in parallel spaced relationship on either side of the patient 22. The lower edges of side plates 24 are adapted to fit into the groove 26 defined by the pairs of guide rails 16 on either side of back plate 12.

As can thus be seen, when assembled, the side plates 24 and back plate 12 essentially form the bottom and two sides of a box-like structure wherein the patient 22 is positioned. A longitudinal working axis 28 passing through the length of the patient therefore, is parallel to both the back plate 12 and the side plates 24.

In addition to the two side plates 24, upper assembly 14 includes a power plate 30 connected between the two side plates 24 and normal to the working axis 28. For added rigidity, a pair of phenolic rods 32 are also connected between side plates 24 on either side of and parallel to the power plate 30.

Figure 3:
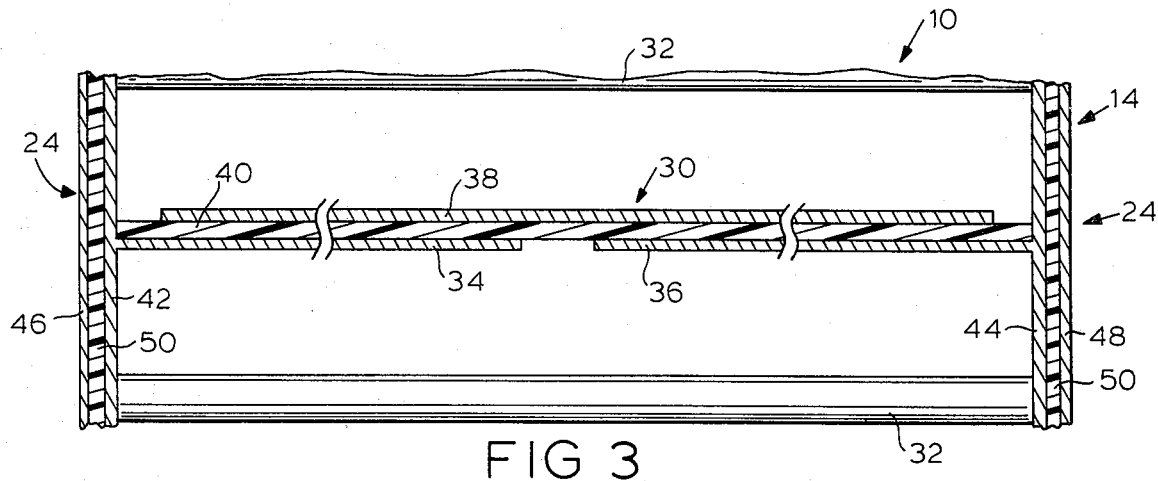
FIG. 3 is a cut-away top view of the electrode of FIG. 1 in the plane III—III.

As can best be seen with reference to FIGS. 1 and 3, the power plate 30 is comprised of three conductive metallic plates 34, 36, 38 separated by a sheet of dielectric material 40 such as polytetrafluoroethylene. Plates 34 and 36 are connected at one end respectively to plates 42 and 44 of side plates 24. These are electrical connections and can be accomplished easily by welding. The two plates 34, 36 are in end-to-end spaced relationship at the opposite ends. Plate 38 is in non-contacting relationship with plates 42, 44. Thus, plates 34, 36, 38 in combination with dielectric material 40 form the two capacitors labelled "C4" and "C3" of FIG. 5.

A similar construction is employed with respect to the side plates 24. This can best be understood with reference to FIGS. 3 and 4 in combination. Plates 42, 44 are spaced from outer plates 46, 48 by dielectric material 50. Dielectric material 50 is also of polytetrafluoroethylene. With particular reference to FIG. 4, plates 42, 44 do not extend all the way to back plate 12 or guide rails 16. Only dielectric material 50 and outer plates 46, 48 fit within the grooves 26 to establish electrical contact with back plate 12. By so doing, plates 42, 44 and outer plates 46, 48 in combination with dielectric material 50 form the capacitors labelled "C1" and "C2" of FIG. 5. To provide a certain springiness within groove 26 to effect electrical contact along the entire length, the guide rails 16 on either side adjacent dielectric material 50 are fitted with a generally U-shaped trim covering 51 of plastic such as is generally available as decorative edging.

As thus constructed, the electrode 10 as hereinbefore described has the equivalent circuit shown in FIG. 6. In use, radio frequency electrical energy is connected thereto across any one of the capacitors C1–C4. The process of coupling radio frequency energy into such an electrode is described in detail in my above-mentioned patent and forms no part of the present invention per se.

As can be seen, the side plates 24 taper from about four inches in width adjacent the top of the power plate 30 to about 17 inches at the connection to the back plate 12. Moreover, as previously described, the back plate is 30 inches long. The current density and resultant magnetic field in these large areas in the side plates 24 and across the connecting traverse back plate 12 is thus minimized. This geometry concentrates the magnetic field through the upper portion, i.e. power plate 30.

FIGS. 7–11 illustrate the tested performance of the present invention by showing the concentration of energy in the region of the power plate 30. As may be seen, if the patient 22 is positioned very close to the power plate 30, the relative energy level is maximum and drops off very rapidly on either side. If a spacing of say 3 to 6 inches is maintained between the power plate 30 and the patient 22, then the energy level is distributed to wider longitudinal dimensions on either side of the traverse member. This provides a further choice of the patient treatment schedule and flexibility. To provide this continuous spacing, the edge of the power plate 30 adjacent the patient is arcuate in shape as shown in FIG. 1. This provides for relatively constant spacing between the power plate 30 and the torso of the patient 22.

Note also from FIG. 2 that the back plate 12 extends in both directions along the longitudinal working axis 28 from the basic resonant circuit. This is done to minimize the inductance beneath the patient and, thereby, distributes the field below the patient over a large area.

Figure 12:
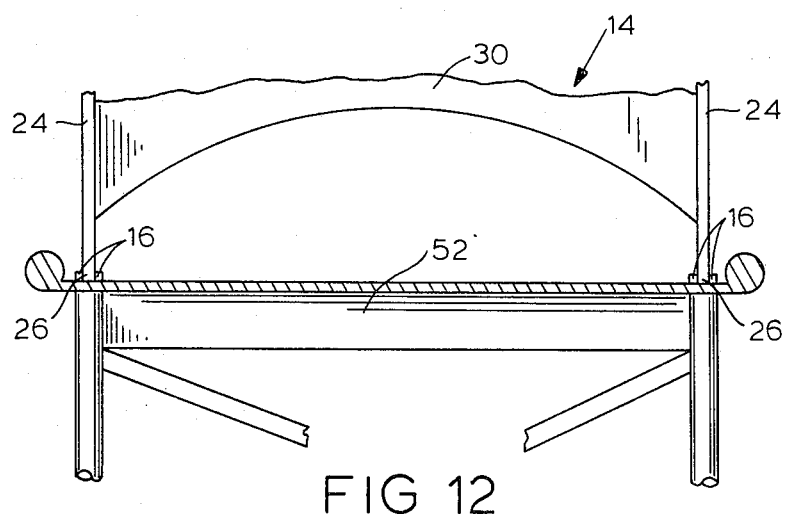
FIG. 12 is a simplified partially cut-away drawing of an alternate embodiment of the present invention wherein the top of a table-like piece of medical apparatus such as a gurney cart is employed as the back plate of the electrode.

As will be noted with reference to the drawings and discussion above, all the capacitances incorporated within the electrode 10 to make it self-resonant, are incorporated in the side plates 24 and power plate 30. The back plate 12 comprises only a single plate of electrically conducting material which is electrically connected to the outer plates 46, 48 of side plates 24. Any metallic plate area can, therefore, be used as back plate 12. Thus, the upper assembly 14 can be used in combination with many table-like pieces of medical apparatus by the mere addition of the guide rails 16 to that apparatus to assure electrical connection to the apparatus along the entire length of the connection edges of side plates 24. For example, with reference to FIG. 12, the upper assembly 14 is mounted on a gurney cart 52 to which the guide rails 16 have been attached. Such apparatus provides a semi-portability. That is, the entire apparatus need not be brought to the patient, but, on the other hand, having once moved the patient to a metal gurney, the patient can be treated with the electrode 10 of the present invention by allowing him or her to remain on the gurney cart 52 and merely placing the upper assembly 14 in electrical contact as shown in FIG. 12.

Thus, it can be seen that the electrode of the present invention provides its desired objectives of portability, convenience, and localized heating.

Wherefore, having thus described my invention, I claim:

1. In an electrode adapted for operative connection to a source of radio frequency energy for use in the treatment of animal tissue by hyperthermia comprising a plurality of electrically interconnected plate members each having at least a pair of plates of electrically conductive material disposed in overlapped relationship with dielectric material disposed between the overlapped portions and wherein the electrically interconnected plate members form a self-resonant single turn loop, the improved electrode comprising:
  (a) a pair of side plate members disposed in parallel spaced relationship with a longitudinal working axis therebetween and parallel to both said side plate members;
  (b) a power plate member disposed between said side plate members in electrical contact with said side plate members and being on one side of said working axis and normal thereto; and,
  (c) a back plate of electrically conductive material disposed between said side plate members on the other side of said working axis and parallel thereto, said back plate being electrically connected to both of said side plate members to thereby complete the self-resonant single turn loop.

2. The improved electrode of claim 1 wherein: said power plate member is arcuate on the edge thereof adjacent said working axis.

3. The improved electrode of claim 1 wherein:
  (a) said side plate members taper from a width of at least 4 d on the edge adjacent said back plate to a width of d adjacent the edge opposite said back plate; and,
  (b) said back plate is at least 4 d wide.

4. The improved electrode of claim 1 wherein: said side plate members are releasably attached to said back plate.

5. The improved electrode of claim 4 wherein:
  (a) said back plate is the metallic top of a table-like piece of medical apparatus; said apparatus additionally having,
  (b) electrical connection means for gripping the edges of said side plate members and for establishing electrical contact along the entire length thereof.

6. The improved electrode of claim 5 wherein: said piece of medical apparatus is a gurney cart.

7. In an electrode adapted for operative connection to a source of radio frequency energy for use in treatment of animal tissue by hyperthermia, the improved electrode comprising:
  (a) a horizontal back plate of electrically conductive material;
  (b) a pair of first side plates of electrically conductive material disposed vertically in parallel spaced relationship and in electrical contact with said back plate, said first side plates being spaced sufficiently to allow the animal tissue to be placed therebetween;
  (c) a pair of second side plates of electrically conductive material disposed between said first side plates in close-spaced parallel relationship to respective ones thereof and having dielectric material between each of said first and second side plates;
  (d) a pair of first power plates of electrically conductive material normal to said second side plates and to said back plate, each of said first power plates being electrically connected on one end to a respective one of said second side plates, said first power plates being disposed to lie in a common plane with their other ends in spaced end-to-end relationship, and spaced from said back plate sufficiently to allow the animal tissue to be placed therebetween; and,
  (e) a second power plate of electrically conductive material disposed in overlapped, close-spaced, parallel relationship to said first power plates and having dielectric material therebetween.

8. The improved electrode of claim 7 wherein: said pair of first plates and said second power plate are in combination arcuate on the edge thereof adjacent the animal tissue.

9. The improved electrode of claim 7 wherein:
  (a) said first side plates and said second side plates taper from a width of at least 4 d on the edge adjacent said back plate to a width of d on the edge opposite said back plate; and,
  (b) said back plate is at least 4 d wide.

10. The improved electrode of claim 7 wherein: said first and second side plates are releasably attached to said back plate.

11. The improved electrode of claim 10 wherein:
  (a) said back plate is the metallic top of a table-like piece of medical apparatus; said apparatus additionally having,
  (b) electrical connection means for gripping the edges of said first side plates and for establishing electrical contact along the entire length thereof.

12. The improved electrode of claim 11 wherein: said piece of medical apparatus is a gurney cart.

* * * * *